United States Patent [19]
Grabenkort et al.

[11] Patent Number: 5,682,874
[45] Date of Patent: *Nov. 4, 1997

[54] SYSTEM FOR CONNECTING AN INHALATION AGENT CONTAINER TO A VAPORIZER

[75] Inventors: Richard W. Grabenkort, Barrington; Sheldon M. Wecker, Libertyville, both of Ill.

[73] Assignee: Abbott Laboratories, Abbott Park, Ill.

[*] Notice: The term of this patent shall not extend beyond the expiration date of Pat. No. 5,427,145.

[21] Appl. No.: 408,461

[22] Filed: Mar. 22, 1995

Related U.S. Application Data

[63] Continuation of Ser. No. 125,064, Sep. 21, 1993, abandoned.
[51] Int. Cl.⁶ .................. A61M 11/00; A61M 16/00; A62B 9/04; C08B 3/00
[52] U.S. Cl. .................. 128/200.14; 128/202.27; 128/203.26; 128/202.22
[58] Field of Search .................. 128/202.22, 202.27, 128/203.12, 203.19, 203.21, 205.21, 200.14, 203.26, 203.27, 203.16, 203.17, 200.24

[56] References Cited

U.S. PATENT DOCUMENTS

| | | | |
|---|---|---|---|
| 4,867,212 | 9/1989 | Mohr et al. | 128/203.12 |
| 4,883,049 | 11/1989 | McDonald | 128/202.22 |
| 5,287,898 | 2/1994 | Falb et al. | 128/200.14 |
| 5,381,836 | 1/1995 | Braatz et al. | 128/200.21 |
| 5,427,145 | 6/1995 | Grabenkort | 604/283 |

*Primary Examiner*—Kimberly L. Asher
*Attorney, Agent, or Firm*—Brian R. Woodworth

[57] ABSTRACT

A reusable connector is provided for mounting on an anesthetic vaporizer to connect the vaporizer with an anaesthetic container and hold the container in an inverted orientation. Cooperating engaging structures are employed to pull the container and connector together. In a preferred form, the container has a closure defining at least one port occluded by a recessed, pierceable membrane. A screw thread is provided on the container. The connector has a base provided with a first coupling for connecting the base to the vaporizer. The base has a second coupling that includes plug adapted to be connected to the container closure, The base also defines a passage extending from the plug through the first coupling for communicating with the vaporizer, The plug includes at least one projecting conduit that communicates with the passage and that defines a piercing tip for entering into the port to pierce the membrane, A collar is mounted for rotation on the base, The collar engages the base and defines a screw thread for engaging the thread on the container to pull the container onto the plug as the membrane is pierced.

2 Claims, 3 Drawing Sheets

Fig. 5
Fig. 6
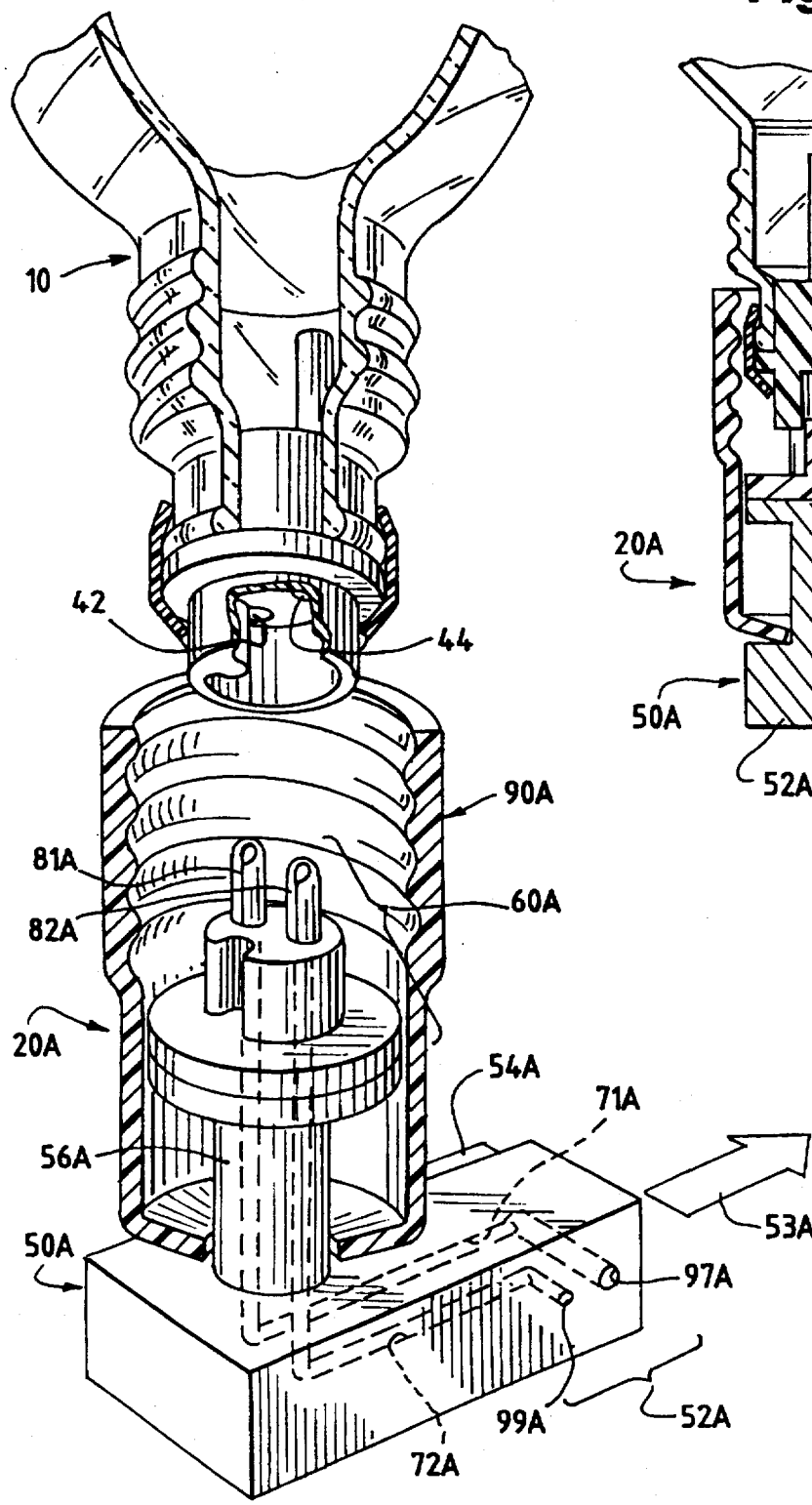
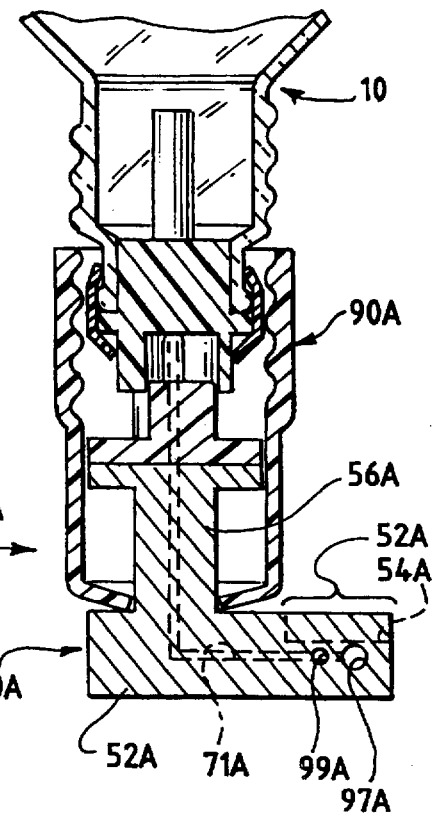

SYSTEM FOR CONNECTING AN INHALATION AGENT CONTAINER TO A VAPORIZER

This is a continuation of application Ser. No. 08/125,064, filed Sep. 21, 1993 now abandoned.

TECHNICAL FIELD

The present invention relates to a system for connecting a container to a device into which the container contents are to be transferred. The system is particularly well-suited for use in operating rooms to safely transfer an anesthetic from a container to a vaporizer while minimizing the likelihood of the anesthetic escaping to the atmosphere.

BACKGROUND OF THE INVENTION AND TECHNICAL PROBLEMS POSED BY THE PRIOR ART

Inhalable anesthetics are typically volatile substances with relatively low boiling points and high vapor pressures. They can be highly flammable and explosive substances in both their liquid and vapor states. Further, inhalation of the vapor by personnel using them can cause drowsiness.

Therefore, such anesthetics must be safely handled in operating rooms in order to minimize the risk of inhalation by medical personnel as well as to minimize the risk of fire or explosion. Preferably, the anesthetic should be used in a way which will ensure that there is little or no release to the atmosphere at all stages of handling during normal surgical procedures.

Anesthetics are typically dispensed in liquid form to an apparatus, such as an anesthetic vaporizer, which mixes the anesthetic with carrier gases, normally oxygen and nitrous oxide. The mixture is supplied in gaseous form to the patient for inhalation.

Devices have been designed for the transfer of an anesthetic from a supply container to a level-controlled reservoir in a vaporizer through a closed system that eliminates the escape of an anesthetic gas to the atmosphere. The devices are designed so that during set-up and disassembly procedures, a supply container of anesthetic is not open and exposed to the atmosphere in the operating room.

One system which has been developed for connecting an anesthetic container to a vaporizer employs a connector tube having adapters at both ends. The tube is flexible and is kink-resistant. The vaporizer end of the tube is provided with a vaporizer adaptor that engages with an anesthetic vaporizer. The end of the tube attached to the anesthetic container is provided with a closure adaptor that engages with a closure on the anesthetic container.

The closure is preferably connected to the supply container prior to use in the operating room. The container closure has a frangible seal adapted to be perforated by a piercing means within the closure adaptor as the adaptor is engaged with the closure. Following perforation of the frangible seal by the piercing means, the closure adaptor and closure remain held together in a snap fit, and this permits the transport of anesthetic through the tube from the supply container to the vaporizer. The system remains closed to the atmosphere throughout the assembly or disassembly procedures.

In order to provide even more assurance that the seal connection remains leak-tight, it would be desirable to provide an improved system for effecting engagement of the container and a connector and for retaining the two parts together. Further, it would be advantageous to provide a means for generating a mechanical advantage when effecting initial engagement between a connector and seal, as well as when piercing the seal. This would facilitate the establishment of the connection and permit the use of engaging structures that are subjected to greater frictional forces for creating superior leak-tight seals.

There are other aspects of conventional connectors that could be improved. For example, a person using a conventional, flexible connector tube must take further action after the container is attached with the flexible connector tube to the vaporizer. Specifically, the person (e.g., the anesthesiologist) must then locate the anesthetic container in an elevated, inverted position and then hold it there as the liquid anesthetic drains from the container, through the flexible tube, and into the vaporizer reservoir. It may take about a minute or more for the container to empty completely.

The flexible tube does not have a self-maintained position for holding the container in the inverted orientation. Thus, the person holding the draining container is not free to attend to other tasks while the container is draining into the vaporizer. It would be desirable to provide an improved connector that does not require a person to hold the container at a particular elevation during the length of time that it takes the container to empty.

Further it would be desirable to accommodate a container having a capacity greater than that of the vaporizer reservoir. It would thus be advantageous to provide a combination connector and holder for such a larger capacity container to maintain the container in an inverted position on the connector. Then the liquid anesthetic could drain into the level-controlled reservoir of the vaporizer as needed. This would effectively increase the capacity of the vaporizer. That would minimize the danger of improper monitoring of a vaporizer during a medical procedure which could result in the vaporizer running out of anesthetic.

Some types of vaporizers are intended for use with only a specific anesthetic or anesthetics. In such situations, care must be taken to insure that only the proper anesthetic is dispensed into the particular vaporizer. Connecting devices have been designed with keying systems to prevent the use of a vaporizer with an anesthetic for which it is not designed.

In particular, the anesthetic container closure has a specific shape, and the connector tube closure adaptor has a complementary shape for mating with the container closure. At the other end of the container tube, the adaptor has a special shape for mating with a complementary portion of the vaporizer anesthetic inlet port. Because the container for each type of anesthetic has its own special closure shape, and because the corresponding connector device fits only the type of vaporizer designed for that anesthetic, the probability of inadvertently using an anesthetic in an incompatible vaporizer, or of administering an incorrect anesthetic to a patient, is greatly reduced, if not eliminated.

Although such keyed, connector tubes function satisfactorily, there are inventory, installation, and management considerations associated with their use. In particular, such connector tubes are typically provided to the user initially unattached to the vaporizer or the anesthetic container. Thus, such connector tubes must be stored and maintained at an appropriate location for use, and such connector tubes can become misplaced.

Because such connector tubes are not inexpensive, it would be desirable to provide an improved connector device that is less likely to be misplaced. Further, it would be advantageous to provide an improved system which is less expensive and even easier to use.

The present invention provides an improved, reusable connector which can accommodate designs having the above discussed benefits and features.

SUMMARY OF THE INVENTION

A reusable connector suitable for mounting on an anesthetic vaporizer is provided for connecting the vaporizer with an anesthetic container. According to one aspect of the invention, the connector has a base with a first coupling which can be permanently or temporarily mounted to the vaporizer. The base has a second coupling which can be attached to the container to hold the container in a generally inverted orientation. The base may be a rigid, unitary member. Alternatively, the base may be a multi-piece structure which can be arranged in a self-maintained configuration for holding the inverted container in the proper orientation for draining into the vaporizer. A suitable leak-tight seal is provided between the container and connector.

The connector defines a passage for permitting the liquid anesthetic to drain from the container into the vaporizer reservoir as needed to maintain the level in the reservoir. The capacity of the container may significantly exceed the capacity of the reservoir. Because the liquid anesthetic can drain into the level-controlled reservoir as needed, the capacity of the reservoir is effectively increased.

According to another aspect of the invention, a mechanical coupling system is employed to apply oppositely acting axial forces to pull the container and connector together, and to retain the container mounted on the connector in a leak-tight fashion. In a preferred form, the connector includes a piercing conduit and is used with a container having at least one port that is occluded by a recessed, pierceable membrane.

The mechanical coupling system includes mating engaging structures on the connector and container. Preferably, a mechanical coupling component, such as a rotatable collar with an engaging structure in the form of a screw thread, is provided on the base second coupling. A mating, engaging screw thread is provided on the container.

Preferably, the base second coupling also has a plug adapted to be connected to the container closure. The base defines a passage extending from the plug through the coupling for communicating with the vaporizer. The plug includes at least one projecting conduit that communicates with the passage and that defines a piercing tip for entering into the port to pierce the membrane. The size and shape of the conduit adjacent the tip are designed to establish an effective, liquid-tight seal around the conduit at the port as the tip pierces the membrane.

When the threaded collar is engaged with the container thread and rotated, the container is pulled onto the plug conduit. As increasing threaded engagement is established, the piercing of the membrane is effected.

Numerous other advantages and features of the present invention will become readily apparent from the following detailed description of the invention, from the claims, and from the accompanying drawings.

BRIEF DESCRIPTION OF THE DRAWINGS

In the accompanying drawings that form part of the specification, and in which like numerals are employed to designate like parts throughout the same, FIG. 1 shows the connector prior to establishment of the connection between the container and vaporizer and shows portions of the components cut away to illustrate interior detail;

FIG. 5 is a fragmentary, perspective view of an alternate embodiment of a system according to the present invention for connecting an anesthetic vaporizer with a connector to an anesthetic container, and FIG. 5 shows the connector prior to establishment of the connection between the container and vaporizer and shows portions of components cut away to illustrate interior details; and FIG. 6 is a cross-sectional view of the connector partially engaged with the container closure.

DESCRIPTION OF THE PREFERRED EMBODIMENTS

The present invention provides a novel system for connecting an anesthetic container to a vaporizer. The system includes a connector which can be maintained in place on the vaporizer and which includes safety key features so that the vaporizer can be connected only to a container of anesthetic for which the vaporizer has been designed.

The system is relatively inexpensive and easy to use. Connecting an anesthetic container to the vaporizer with this system results in the anesthetic draining directly to the vaporizer in a closed system that eliminates the escape of anesthetic to the atmosphere.

While this invention is susceptible of embodiment in many different forms, this specification and the accompanying drawings disclose only some specific forms as examples of the invention. The invention is not intended to be limited to the embodiments so described, however. The scope of the invention is pointed out in the appended claims.

For ease of description, the system components of this invention are described in the normal operating position, and terms such as upper, lower, horizontal, etc., are used with reference to this position. It will be understood, however, that the components of this invention may be manufactured, stored, transported, and sold in an orientation other than the position described.

Figures illustrating the components of the invention show some mechanical elements that are known and that will be recognized by one skilled in the art. The detailed descriptions of such elements are not necessary to an understanding of the invention, and accordingly, are herein presented only to the degree necessary to facilitate an understanding of the novel features of the present invention.

Figure 1:
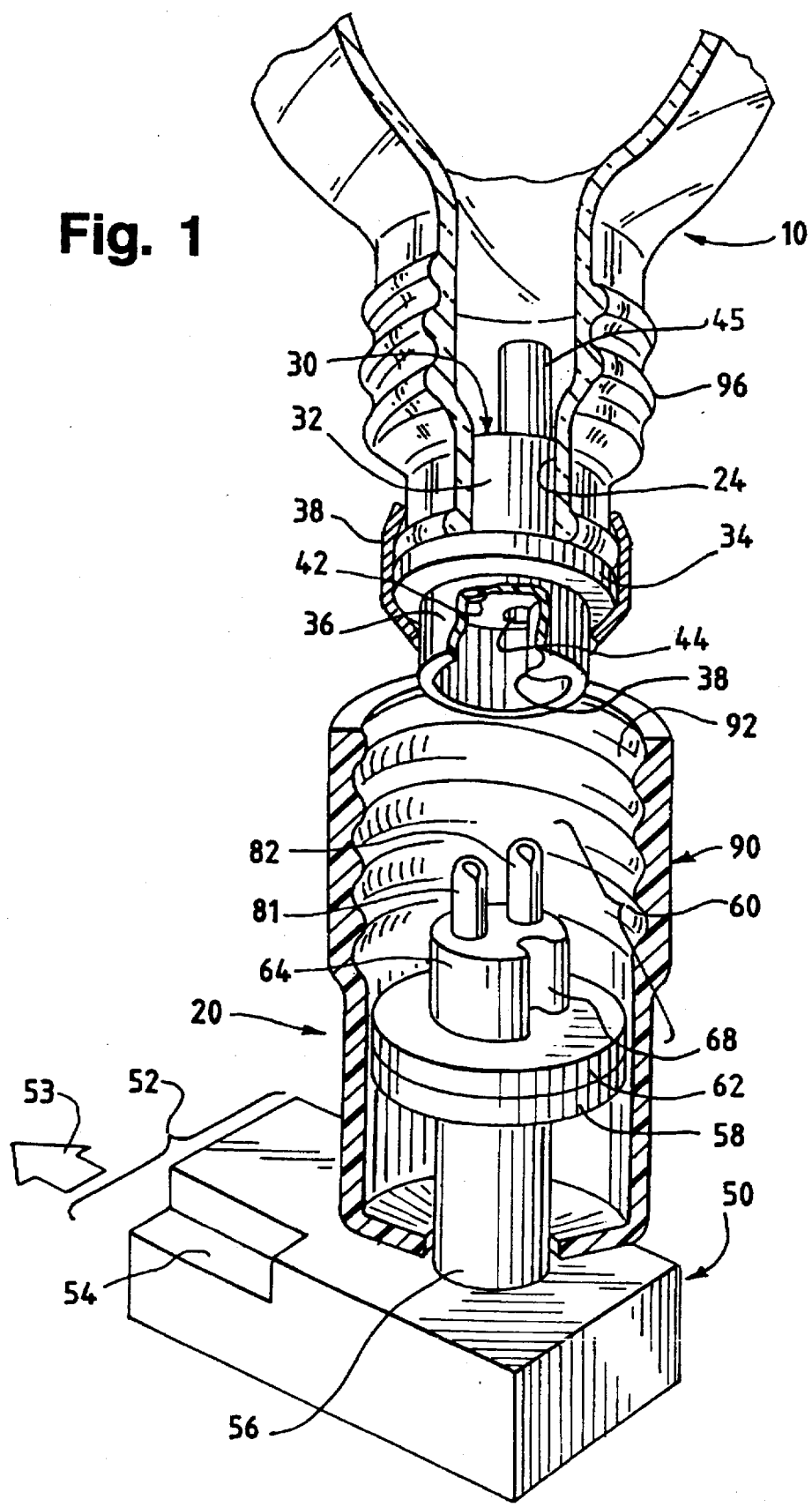
FIG. 1 is a fragmentary, perspective view of a system according to the present invention for connecting an anesthetic vaporizer with a connector to an anesthetic container that has a closure adapted to mate with the connector.

FIG. 1 illustrates a system for connecting an anesthetic container to a vaporizer (not shown) with a novel connector 20. The container 10 is shown inverted, and the container 10 typically contains anesthetic in a liquid state (not visible) which drains from the container 10 into the vaporizer to fill the vaporizer.

The container 10 defines an opening 24 (FIG. 1) which is sealed with a closure 30. The closure 30 may be molded from a resilient material (such as polyethylene) and frictionally engaged with the container 10 at the opening 24. If desired, an adhesive or sealant compound could be applied to the interior of the container 10 in the opening 24 just prior to mounting of the closure 30 in the container 10.

The closure 30 includes a cylindrical inner portion 32 and a larger diameter, outer flange 34. The flange 34 is adapted to seat against the end of the container 10. Preferably, a sealing sleeve, band, or ferrule 38 is applied around the end of the container 10 and the closure flange 34 to insure an effective seal. The sleeve or band 38 may be a shrink fit material that has been shrunk into tight engagement with the exterior of the container 10 and closure flange 34.

The closure 30 also includes a collar 36 projecting outwardly from the flange 34 to define a receiving socket. An inside portion of the collar 36 defines a predetermined key or shaped structure, such as a rib 38.

The closure 30 provides access to the interior of the container 10 through two ports 42 and 44. Port 42 functions as a discharge passage to drain the liquid anesthetic from the container 10, and port 44 functions as a vent passage for admitting gas into the container as the liquid contents discharge from the container through the port 42. To aid in the venting process, the closure 30 defines an inwardly projecting tube 45 which defines a continuation of the port 44.

Figure 3:
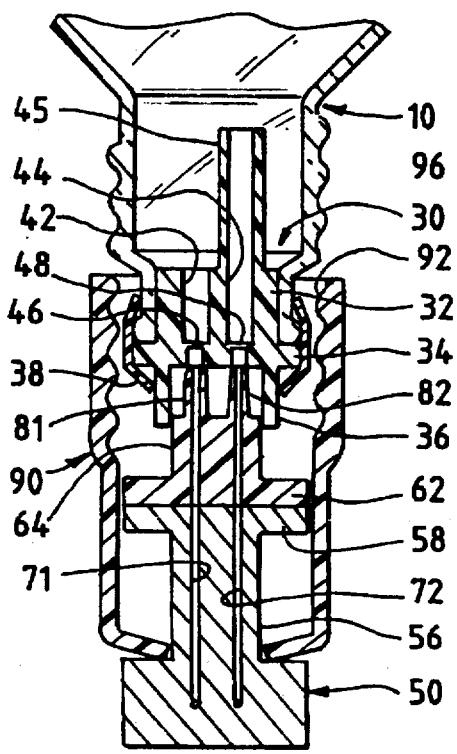
FIG. 3 is a cross-sectional view taken generally along the plane 3—3 in FIG. 2.

In the initially manufactured condition, the closure 30 does not permit flow through the ports 42 and 44. To this end, the port 42 is occluded by a recessed, pierceable diaphragm or membrane 46 (FIG. 3), and the port 44 is occluded by a recessed, pierceable diaphragm or membrane 48 (FIG. 3).

The connector 20 has a preferably rigid, generally L-shaped base 50. One end of the base 50 is a first connecting portion or first coupling 52 for connecting the base 50 to the vaporizer (not shown). In the embodiment illustrated, the base coupling 52 defines a notch 54 which functions as a predetermined shape or key for mating with a corresponding or complementary structure (not illustrated) on the vaporizer.

The connector 20 is initially mounted to the vaporizer by pushing the connector endwise (in the direction of the arrow 53 in FIG. 1) into the vaporizer inlet port. A vaporizer designed for one type of anesthetic would have a particular configuration or key at its inlet port for mating with only one specific coupling shape of a connector. In this way, only a connector intended for one type of anesthetic can be connected to a vaporizer designed for that anesthetic.

The connector base 50 includes an outwardly projecting leg 56 which terminates in a flange 58 at a second coupling that includes a plug 60 extending from the flange 58.

The plug 60 includes a flange 62 connected to, and mating with, the flange 58. The plug 60 further includes a boss 64 which extends from the flange 62 and is adapted to be received in the socket defined by the container closure collar 36. A peripheral portion of the boss 64 defines a recess 68 which has a shape that is complementary to, and that is adapted to mate with, the rib 38 on the container closure collar 36.

Figure 2:
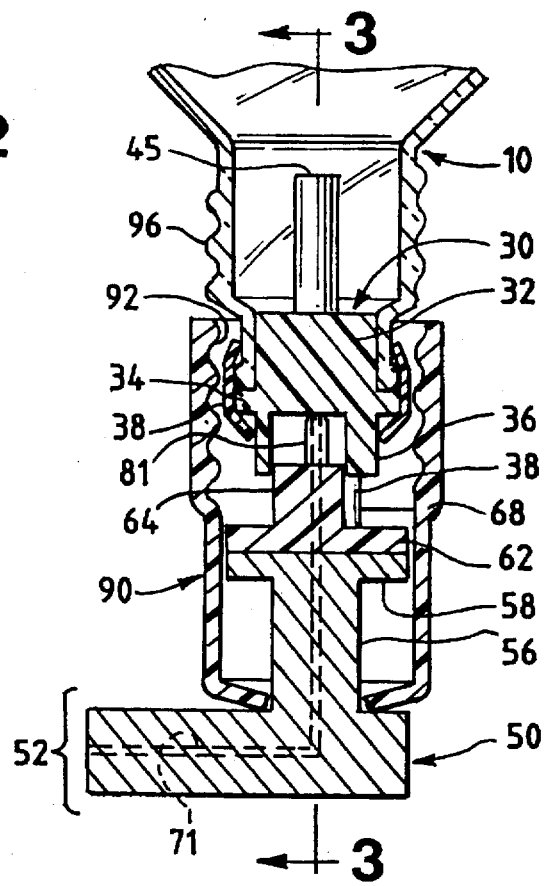
FIG. 2 is a cross-sectional view of the connector partially engaged with the container closure.

As illustrated in FIGS. 2 and 3, the base 50 defines a first passage 71 and a second passage 72 which each extend from the plug 60 through the base coupling 52 for communicating with the vaporizer. The plug 60 includes a first projecting conduit 81 communicating with the passage 71 and defining a piercing tip for entering into the closure port 42 to pierce the membrane 46. The plug 60 also defines a second projecting conduit 82 communicating with the passage 72 and defining a piercing tip for entering into the closure port 44 to pierce the membrane 48.

The plug 60 is adapted to engage the container 10 after the connector 50 has been properly connected with the vaporizer (not shown). As illustrated in FIGS. 2 and 3, the inverted container 10 can then be located to align the socket of the closure collar 36 with the connector plug boss 64. The rib 38 on the closure 30 is aligned with recess 68, and the ports 42 and 44 are aligned with the piercing conduits 81 and 82, respectively. Then, the container 10 can be pushed downwardly slightly so that the piercing conduits 81 and 82 begin to enter the ports 42 and 44, respectively.

The size and shape of each conduit 81 and 82 adjacent its tip is effective to establish a liquid-tight seal around the conduit at the port as the tip begins to engage the membrane (46 or 48). The proper and complete downward displacement of the container 10 relative to the connector 20 is effected by a novel coupling system which includes a collar 90 on the connector 20. The collar 90 is part of the connector second coupling and is disposed for rotation on the connector leg 56.

Figure 4:
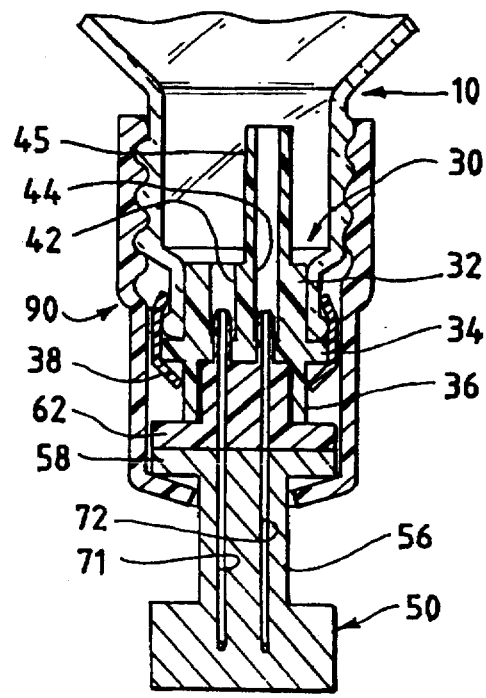
FIG. 4 is a cross-sectional view similar to FIG. 3 and shows the connector fully engaged with the closure of the anesthetic container.

The inner end of the collar 90 is adapted to engage the connector base flange 58 (FIG. 4). The interior of the collar 90 defines an engaging structure, such as a screw thread 92. The container defines a cooperating engaging structure, such as a mating screw thread 96. Alternatively, the mating screw thread 96 could be provided on the exterior of the closure 30 outwardly of the container 10 (and the collar 90 would have to be configured as necessary to properly engage such a screw thread on the closure).

As the threaded, swivel collar 90 is engaged with the container thread 96 and tightened on the container 10, the closure ports 42 and 44 are pulled onto the plug conduits 81 and 82, respectively, and the membranes 46 and 48 are pierced. The membranes 46 and 48 are sufficiently recessed so that they are not ruptured until after a liquid-tight seal is effected between the plug conduits 81 and 82 and the mating portions of the ports 42 and 44 which are exterior of the membranes 46 and 48.

Typically, the closure material, at least in the region of the ports 42 and 44 exterior of the membranes 46 and 48, is somewhat resilient. Further, the diameters of the ports 42 and 44 exterior of the membranes 46 and 48, respectively, are less than the maximum exterior diameters of the conduits 81 and 82, respectively. This ensures the formation of tight seals just prior to, as well as after, the piercing of the membranes 46 and 48.

Preferably, the membranes 46 and 48 are formed as unitary portions of the closure. It is presently contemplated that the preferred closure will be molded as the unitary structure from a suitable thermoplastic material (e.g., polyethylene). The pierceable membranes 46 and 48 are preferably molded as part of the closure in the form of generally round, frangible disks or diaphragms.

When the container 10 has been properly attached to the connector 20, the container is maintained by the connector 20 in an inverted position. No person need hold the container 10 in place. The liquid anesthetic in the container 10 drains through the port 42 and passage 71 into the vaporizer. Air or other gas within the vaporizer can vent up through the passage 72 and closure port 44 into the container 10 to facilitate proper and complete draining of the container 10.

The level of the anesthetic liquid in the vaporizer reservoir is controlled by the vaporizer. Fresh anesthetic liquid can flow into the reservoir from the container 10 as needed. Thus, a container having a capacity greater than the vaporizer capacity may be employed.

When the container 10 is empty, the filler port valve on the vaporizer can be closed. Then the empty container 10 can be unscrewed from the connector 20, and the empty container 10 can be removed for disposal. An auxiliary cover (not illustrated) could be installed over the end of the empty container if desired.

Because the connector 20 can remain mounted on the vaporizer, there is little likelihood that the connector 10 will become misplaced or lost. Further, the connector 20 will then be again ready to receive a new anesthetic container. Because the connector 20 is keyed for a particular anesthetic and vaporizer, only the type of anesthetic appropriate for the vaporizer to which the connector is mounted can be used.

If desired, other forms of a mechanical coupling system may be employed to couple the container to the connector. For example, the movable, threaded collar 90 need not be provided on the base second coupling for engaging threads on the container. Rather, the second coupling could include a rotatable, bayonet lock member (not illustrated) for engaging a mating lock member on the container.

Yet another form of the base second coupling could include a pivoting cam lock member (not illustrated) or overcenter arm (not illustrated) for engaging a mating structure on the container. Alternatively, a cam lock member or arm could be provided on the container instead of on the connector, it being understood that the connector would, of course, have a suitable mating engagement structure. Preferably, such alternate coupling systems would not require rotation of the container on the connector so that two, parallel piercing conduits can be used in the connector.

An alternate embodiment of the connector is illustrated in FIGS. 5 and 6. The connector is generally designated therein by reference numeral 20A and is shown in use with the container 10 which has previously been described in detail above with reference to FIGS. 1–4. The embodiment of the connector 20A is preferred for certain types of conventional vaporizers which have a particular arrangement of the liquid inlet and gas outlet ports (not illustrated).

The connector 20A has an exterior configuration that is substantially similar to the configuration of the first embodiment of the connector 20 described above with reference to FIGS. 1–4. Specifically, the connector 20A has a base 50A with an outwardly projecting leg 56A terminating in a plug 60A surrounded by a swivel collar 90A. The plug 60A includes a first projecting conduit 81A and a second projecting conduit 82A. The first conduit 81A is adapted to be received in, and penetrate a membrane within, the container closure port 42. The conduit 82A is adapted to be received in, and penetrate a membrane within, the container closure port 44. The conduits 81A and 82A are hollow and communicate with passages 71A and 72A, respectively, that are defined the base 50A.

Insofar as the features of the connector 20A have been described, they are identical to the features of the first embodiment of the connector 20 described above with the exception of the routing of the passages 71A and 72A in the connector base 50A. Specifically, whereas FIG. 2 shows that the passages (e.g., 71) in the first embodiment of the connector 20 open to the distal end of the base coupling portion 52, the passages 71A and 72A in the second embodiment of the connector 20A do not open directly to the end of the base 50A. Rather, as illustrated in FIGS. 5 and 6, the passages 71A and 72A extend laterally to a side of the base 50A. The passage 71A defines an opening 97A in the base side wall, and the passage 72A defines an opening 99A in the base side wall.

The openings 97A and 99A are located in the coupling portion 52A on the side opposite a notch 54A which functions as a predetermined shape or key for mating with a corresponding or complementary key structure (not illustrated) on the vaporizer. The openings 97A and 99A are adapted to register with corresponding ports in the vaporizer when the base 50A is properly and fully inserted into the vaporizer (in the direction of the arrow 53A as shown in FIG. 5). In all other respects, the connector 20A otherwise functions in a manner identical to that described above for the first embodiment of the connector 20, and the attachment of the connector 20A to the container 10 is effected in the same manner as explained above with respect to the first embodiment of the connector 20.

The connector of the present invention may also be provided with the vaporizer as a permanent or substantially permanent component that is normally not intended to be removed by the vaporizer operator. In some applications, such an installation may provide greater convenience and less handling while facilitating storage.

It will be readily apparent from the foregoing detailed description of the invention and from the illustrations thereof that numerous variations and modifications may be effected without departing from the true spirit and scope of the novel concepts or principles of this invention.

What is claimed is:

1. A system for connecting an anesthetic vaporizer to an anesthetic container to enable transport of an anesthetic therebetween, said system comprising:

a closure constructed to engage an open end of an anesthetic container, said closure defining a first port and a second port therethrough, said first and second ports spaced from one another, said first and second ports occluded by respective first and second recessed, pierceable membranes; and a connector constructed to engage an anesthetic vaporizer, said connector comprising a plug constructed to engage said closure, said plug comprising first and second projections extending therefrom, said first and second projections spaced from one another so as to be simultaneously insertable into said first and second ports defined through said closure, respectively, said connector defining a first passage and a second passage therethrough, said first and second passages extending through said first and second projections, respectively, said first and second projections defining respective first and second apertures therethrough, said first passage in fluid communication with an external environment of said first projection through said first aperture and said second passage in fluid communication with an external environment of said second projection through said second aperture, said first and second projections defining respective first and second piercing tips, said first and second piercing tips constructed to enter said first and second ports, respectively, and pierce said first and second recessed, pierceable membranes, respectively, said connector further comprising a rotatable collar, said rotatable collar defining a screw thread constructed to threadably engage a screw thread defined on an anesthetic container, said screw thread defined on said rotatable collar constructed to cause said closure to be moved toward said connector as said collar is threadably tightened, said screw thread defined on said collar further constructed to cause said first and second piercing tips to pierce said first and second recessed, pierceable membranes, respectively, as said collar is threadably tightened.

2. A system for connecting an anesthetic vaporizer to an anesthetic container to enable transport of an anesthetic therebetween, said system comprising:

- a closure constructed to engage an open end of an anesthetic container, said closure defining a first port and a second port therethrough, said first and second ports spaced from one another, said first and second ports occluded by respective first and second recessed, pierceable membranes, said closure defining a screw thread thereon; and

- a connector constructed to engage an anesthetic vaporizer, said connector comprising a plug constructed to engage said closure, said plug comprising first and second projections extending therefrom, said first and second projections spaced from one another so as to be simultaneously insertable into said first and second ports defined through said closure, respectively, said connector defining a first passage and a second passage therethrough, said first and second passages extending through said first and second projections, respectively, said first and second projections defining respective first and second apertures therethrough, said first passage in fluid communication with an external environment of said first projection through said first aperture and said second passage in fluid communication with an external environment of said second projection through said second aperture, said first and second projections defining respective first and second piercing tips, said first and second piercing tips constructed to enter said first and second ports, respectively, and pierce said first and second recessed, pierceable membranes, respectively, said connector further comprising a rotatable collar, said rotatable collar defining a screw thread for threadably engaging said screw thread defined on said closure, said screw thread defined on said rotatable collar constructed to cause said closure to be moved toward said connector as said collar is threadably tightened to said closure, said screw thread defined on said collar further constructed to cause said first and second piercing tips to pierce said first and second recessed, pierceable membranes, respectively, as said collar is threadably tightened to said closure.

* * * * *

UNITED STATES PATENT AND TRADEMARK OFFICE
CERTIFICATE OF CORRECTION

PATENT NO. : 5,682,874
DATED : November 4, 1997
INVENTOR(S) : Grabenkort et al.

It is certified that error appears in the above-identified patent and that said Letters Patent is hereby corrected as shown below:

In the Abstract, line 11, change "closure," to --closure.--.

In the Abstract, line 13, change "vaporizer," to --vaporizer.--.

In the Abstract, line 16, change "membrane," to --membrane.--.

In the Abstract, line 17, change "base," to --base.--.

Signed and Sealed this

Seventeenth Day of March, 1998

Attest:

BRUCE LEHMAN

Attesting Officer

Commissioner of Patents and Trademarks